United States Patent
Mertens et al.

(10) Patent No.: US 7,294,837 B2
(45) Date of Patent: Nov. 13, 2007

(54) TABLETS PRESS WITH INTEGRAL NIR MEASURING DEVICE

(75) Inventors: Richard Mertens, Laupheim (DE); Heino Prinz, Laupheim (DE)

(73) Assignee: Uhlmann VisioTec GmbH, Laupheim (DE)

(*) Notice: Subject to any disclaimer, the term of this patent is extended or adjusted under 35 U.S.C. 154(b) by 321 days.

(21) Appl. No.: 11/133,830

(22) Filed: May 20, 2005

(65) Prior Publication Data

US 2006/0263461 A1   Nov. 23, 2006

(30) Foreign Application Priority Data

May 27, 2004   (EP) .................................. 04012601

(51) Int. Cl.
*G01N 21/35* (2006.01)
*B30B 11/00* (2006.01)

(52) U.S. Cl. ..................... 250/339.07; 250/339.11; 256/328; 256/72

(58) Field of Classification Search ............. 356/326, 356/328; 250/339.07, 339.11, 341.8; 359/509
See application file for complete search history.

(56) References Cited

U.S. PATENT DOCUMENTS

| | | | |
|---|---|---|---|
| 4,893,253 A | 1/1990 | Lodder | |
| 5,442,437 A | 8/1995 | Davidson | |
| 6,064,056 A | 5/2000 | Doak | |
| 6,079,968 A | 6/2000 | Schmitz et al. | |
| 6,919,556 B1 * | 7/2005 | Laurence | 250/222.2 |
| 7,057,722 B2 * | 6/2006 | Gehrlein et al. | 356/328 |
| 2005/0184435 A1 | 8/2005 | Hinzpeter et al. | |

FOREIGN PATENT DOCUMENTS

EP        0 887 638 A1    6/1997

* cited by examiner

*Primary Examiner*—F. L. Evans
(74) *Attorney, Agent, or Firm*—Bliss McGlynn, P.C.

(57) ABSTRACT

The tablets press according to the invention comprises an integral measuring device for the determination of the quantitative content of at least one substance in a tablet, comprising: at least one radiation source, which emits radiation in the near infrared range, for the irradiation of the tablet, a radiation receiving device contained in a measuring head, which receives the radiation reflected by the tablet, a spectrometer for receiving the radiation from the radiation receiving device and for supplying an output signal according to the intensity of the received radiation at a number of different wavelengths and a device for the quantitative determination of the content of at least one substance contained in the tablet and/or for the determination of the ratios of all or some of the contained components based on the output signal, wherein the measuring device is suitable for measuring each individual pressed tablet, and the trigger times of the measurements are correlated with the conveying speed of the tablets press.

7 Claims, 2 Drawing Sheets

TABLETS PRESS WITH INTEGRAL NIR MEASURING DEVICE

FIELD OF THE INVENTION

Figure 1:
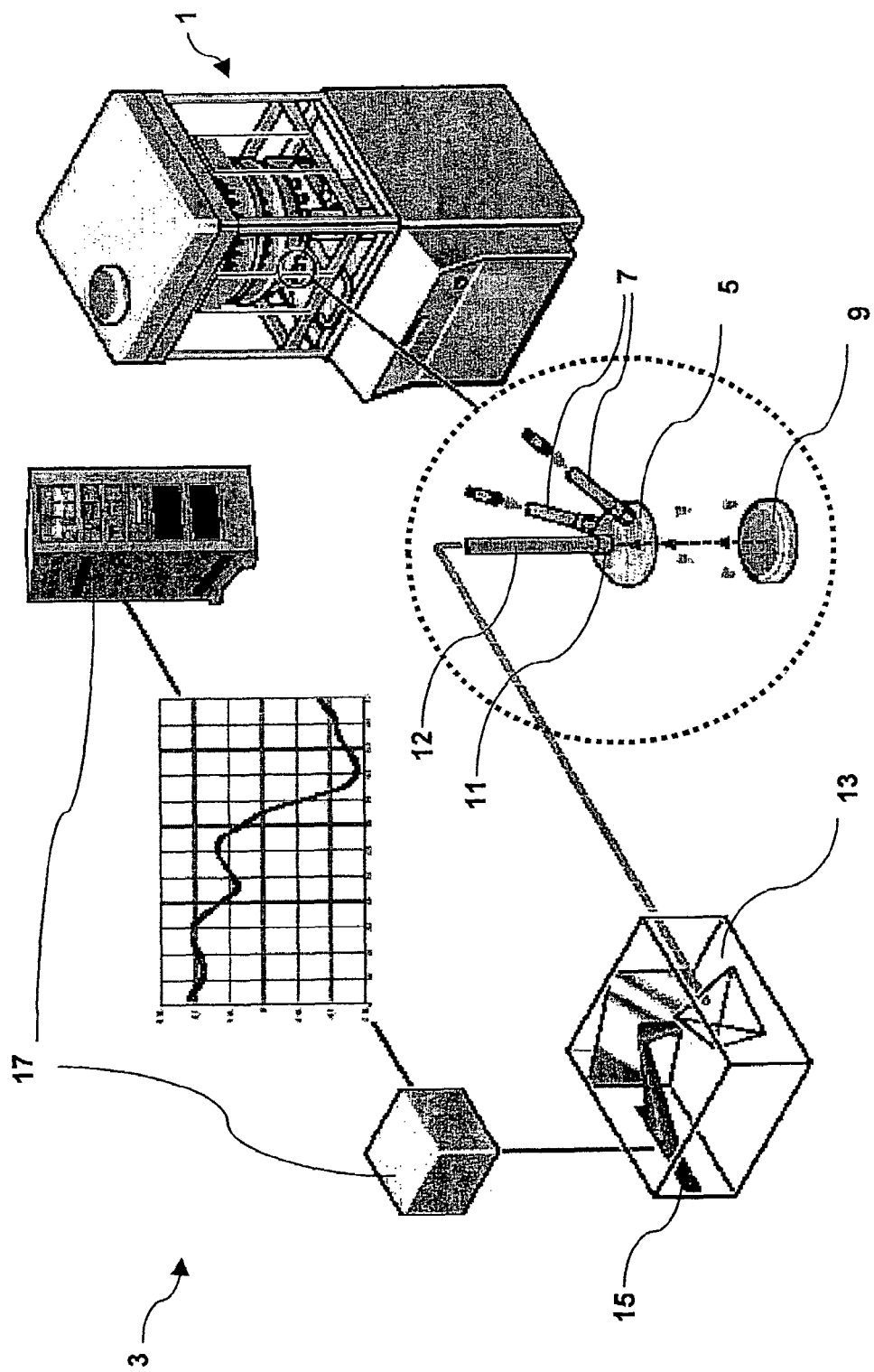

The invention relates to a tablets press for the manufacture of tablets from powder substances.

BACKGROUND OF THE INVENTION

These types of tablets presses are usually formed as rotary tablets presses in which first the press cups occurs are filled with a readily mixed powder substance, then two press punches with a suitable shape press the powder to form a desired tablet shape and the finished tablet is finally ejected and passed on to a packaging station. The capacity of such rotary tablets presses is very high and is normally between 250,000 to 1,000,000 tablets per hour.

In the field of the manufacture of medicaments, apart from the requirement for an increase in productivity, continuous efforts are being made to improve quality control for increasing the safety of medicaments. The manufacture takes place according to the international standard for good manufacturing practice (Current Good Manufacturing Practice, CGMP), which is specified by the medicament monitoring authorities (for example the US Food and Drug Administration, FDA). For severe infringements against this manufacturing practice, the permission to manufacture medicaments can be withdrawn from a company.

An important part of good manufacturing practice is the physical-chemical and microbiological testing and approval of the finished product. In the course of this testing a number of parameters which describe the quality of the product are tested and compared with specifications. The specifications are laid down either in the approval documentation or in the international pharmacopoeias. Once all specifications are satisfied, the product can be marketed. One of these test parameters is the content of the active ingredient which must be determined quantitatively. Another parameter is the hardness of the tablet. The quantitative determination or the hardness determination is normally performed on a random sample basis and in the form of a destructive test chromatographical methods using fluid or gas and also spectroscopic methods are preferably employed as analysis methods, but they sometimes require preparation of the sample. A destructive mechanical strength analysis is carried out for the hardness measurement. These methods have a relatively high precision, but the speed of analysis is very low. Consequently, these methods are not suitable for supplying a result "in-line", i.e. immediately during the manufacturing process.

The disadvantage of the random sample batch test is that trends or unusual incidents within the tablet production cannot be detected. There is the risk that tablets are approved as conforming to the specification, although they in reality do not lie within the approval limits. These "out-of-specification" (OOS) products can for example arise due to short-term production problems.

In principle, spectroscopy in the near infrared range is suitable for a continuous check of product flows. The European patent EP-B-0 887 638 for example describes a method and a device for the analysis of the composition of moving tablets or capsules, wherein a near infrared (NIR) radiation source is used and the NIR light reflected from the tablet is detected and examined. However, in this case speeds of only about 50,000 sample analyses per hour could be achieved, which only enables use with relatively slow conveyor belts.

The object of this invention is to provide a tablets press in which an extremely reliable quality control of the manufactured tablets is simultaneously performed.

SUMMARY OF THE INVENTION

The tablets press according to the invention comprises an integral measuring device for the determination of the quantitative content of at least one substance in a tablet, which comprises at least one radiation source, which emits radiation in the near infrared range, for irradiation of the tablet, a radiation receiving device contained in a measuring head, which receives the radiation reflected by the tablet, a spectrometer for receiving the radiation from the radiation receiving device and for supplying an output signal according to the intensity of the received radiation at a number of different wavelengths and a device for the quantitative determination of the content of at least one substance contained in the tablet or for the determination of the ratios of a number or all of the contained components based on the output signal. The measuring device is suitable for measuring each individual pressed tablet. The trigger times of the measurements are correlated with the conveying speed of the tablets press.

The measuring device quantitatively determines the content of a certain substance using mathematical methods based on the output signal of the spectrometer and is suitable for directly deciding whether or not the measured tablet lies within the predetermined integrity criteria.

The measuring device may also be able to determine the hardness from the content ratios determined using suitable mathematical methods based on the output signal of the spectrometer and may be able to decide whether or not the measured tablet lies within predetermined tolerance criteria.

Advantageously, the spectrometer in the measuring device of the tablets press according to the invention comprises a device for splitting the received radiation into a number of wavelengths for detection by a photodiode array which enables particularly short exposure times.

Preferably, the tablets press according to the invention comprises a radiation source in the near infrared range (800 nm to 2500 nm), for example a mercury halogen lamp.

In order to be able to arrange the radiation source separately from the pressing device, the device according to the invention comprises at least one light guide, which is arranged between the radiation source and the measuring head, and the radiation emitted from the radiation source is guided to the point of measurement, i.e. to the tablet to be measured.

In the same way it is advantageous to arrange at least one light guide, which guides the light reflected from the tablet to the spectrometer, between the measuring head and the spectrometer so that the spectrometer can be arranged outside of the pressing device.

At the input and output of the light guide, respectively, the measuring head preferably comprises a collecting lens for obtaining the largest possible luminous efficiency.

Furthermore, the measuring head can comprise a glass window transparent to NIR to prevent the input and output optical systems from becoming dirty.

A particular advantage is if the glass window which is transparent to NIR comprises a self-cleaning surface, whereby the maintenance effort is noticeably reduced and corruption of the measurement result is prevented.

Alternatively, the measuring head comprises openings for blowing in a curtain of air, whereby the measurement section is kept clear of any particles which might corrupt the measurement.

Alternatively, the measuring head comprises openings for sucking in the ambient air, whereby the measurement section is kept clear of any particles which might corrupt the measurement. Also a combination of a suction and blowing device is possible.

One particular advantage of the tablets press is that the spectrometer is suitable for carrying out a measurement within less than 10 ms, preferably 2 ms. This is achieved, among other things, by the use of the photodiode array which, in addition, comprises the required number of single detector elements securing the demanded high accuracy.

The synchronism of the measurement and evaluation process with the pressing process is achieved especially in that the measuring device is suitable of processing a trigger signal corresponding to the number of tablets passing through the measuring device per time unit.

A further advantage of the tablets press according to the invention is that the trigger times of the measurements can be determined automatically from the speed of the tablets press.

The measuring head of the tablets press is preferably positioned such that the measurement is performed between the release of the tablet by the press punches and the ejection of the tablet.

Further details, features and advantages of this invention are given by the following description with reference to the drawings.

SHORT DESCRIPTION OF THE DRAWINGS

Figure 2:
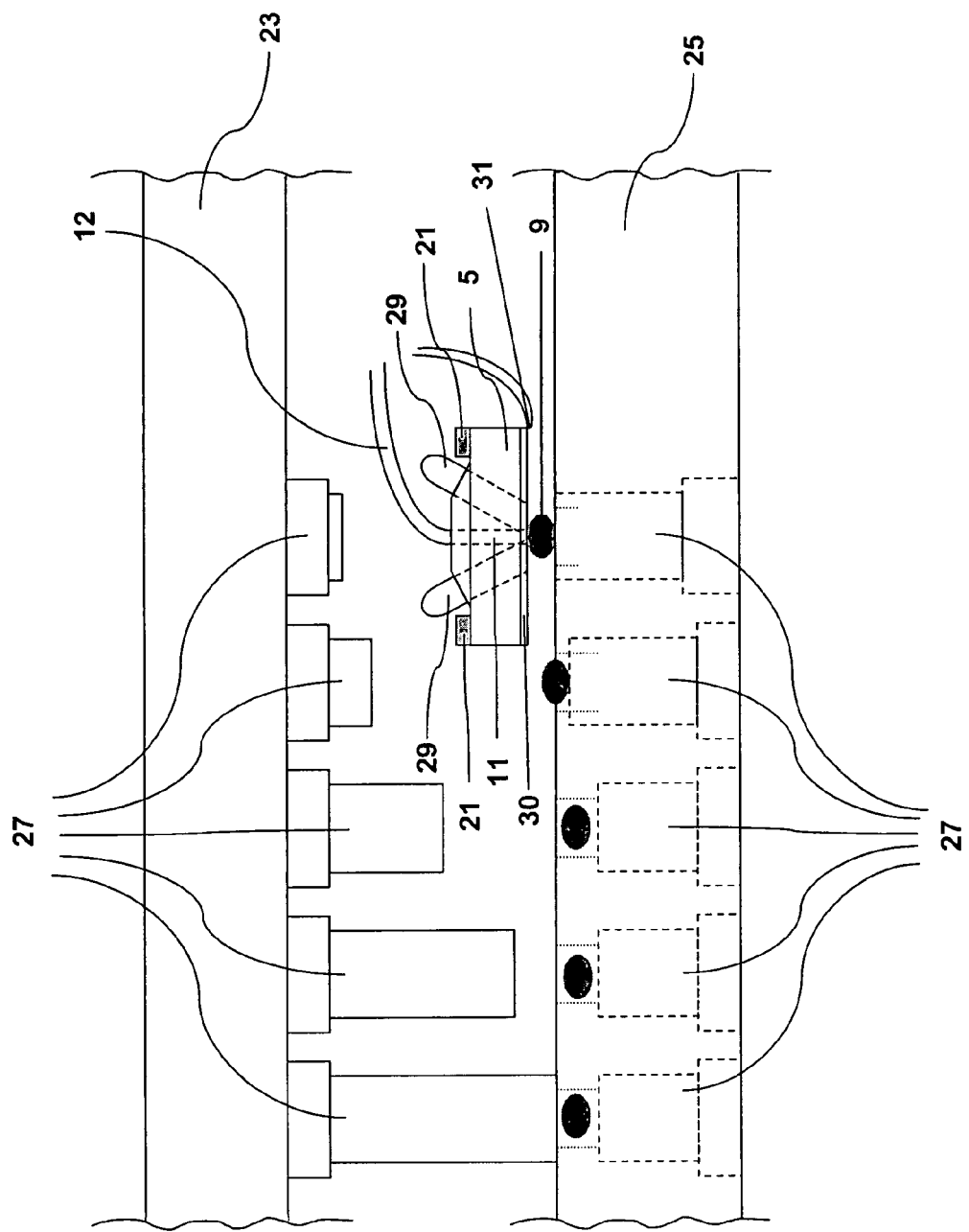

FIG. 1 shows a schematic representation of the tablets press according to the invention with the components of the measuring device; and FIG. 2 shows a schematic cross-sectional view of a preferred embodiment of the device according to the invention.

DETAILED DESCRIPTION OF PREFERRED EMBODIMENTS

FIG. 1 illustrates schematically a preferred embodiment of the tablets press 1 according to the invention. The elements of the integrated measuring device 3 are shown individually for the sake of clarity. The measuring device 1 comprises at least one radiation source (not illustrated in FIG. 1) in the NIR range, for example a mercury halogen lamp or a tungsten halogen lamp. A measuring head 5 is for example arranged stationary within the tablets press 1 in the section between the circulating press punches. The near infrared radiation emitted by the radiation source is guided by, for example, two light guides 7 to the measuring head 5 and from there symmetrically onto the already pressed tablet 9. Alternatively, the radiation sources can also be arranged directly on the measuring head 5 to irradiate the tablet 9 directly via a suitable optical system.

The radiation reflected diffusely from the tablet 9 is received in the radiation receiving device 11, which is also arranged on the measuring head 5, preferably by a collecting lens (not illustrated) and is fed to the spectrometer 13 by a light guide 12. In the spectrometer 13 the reflected radiation, containing the spectral information of the irradiated tablet 9, is split in a known manner into radiation of different wavelengths, for example by using a grid, and is detected by a photodiode array 15. The intensities detected by the photodiode array 15 dependent on the wavelengths are converted into digital signals in the evaluation device 17 by using an A/D converter and are evaluated by a computer. In principle, FTNIR systems or acoustic-optical NIR systems can also be used provided their recording speed and resolution meet the requirements.

FIG. 2 shows a schematic cross-sectional view of a preferred embodiment of the device according to the invention, in which the measuring head 5 is fitted stationary on the tablets press using known fixing elements 21. The upper and lower rotary units 23, 25 comprise a defined number of press punches 27 each having a cross-sectional shape and pressing area to suit the tablet shape. During a rotation of production each single tablet 9 is pressed by the press punches 27 according to a certain pressing scheme so that the tablet 9 comprises a defined final shape before it is ejected. The upper and lower rotary units 23, 25 usually move with a uniform speed. The press punches 27 release the tablet 9 at a defined release position which is identical for each tablet. It is precisely at this position that the stationary NIR irradiation and measurement is carried out by the elements positioned on the measuring head 5.

In the embodiment illustrated schematically in FIG. 2, the radiation sources 29 are arranged directly on the measuring head 5. Alternatively, in a further embodiment, as shown in FIG. 1, the light guides 7 can be arranged at the positions of the radiation sources 29 such that they guide the radiation from a remotely arranged radiation source 29 to the tablet 9. The radiation diffusely reflected from the tablet 9 is partially collected by the radiation receiving device 11 and guided via the associated light guide 12 to the spectrometer 13.

A glass window 30 transparent to NIR can be arranged on the bottom of the measuring head 5 to prevent contamination and thus avoid erroneous measurements due to possible systematic errors. In addition the window 30 can comprise a self-cleaning surface which is realized in nanotechnology. In the same way the measuring head 5 can comprise suitably shaped openings 31, via which a curtain of air can be blown in or air can be drawn out to give protection against contamination. It is thus ensured that the optical elements of the measuring head 5 are subjected to the same continuous measurement conditions.

As already mentioned, the irradiation of each individual tablet 9 is carried out preferably at a stationary point within the rotary tablets press 1, i.e. where the circulating press punches 27 release the fully pressed tablets 9 before they are transported to the next station in the product line. The use of a movable sensor head which moves with the tablet for a few milliseconds is also conceivable. The geometry of the tablets press 1, i.e. the radius of the device and the exact position of the press punches 27 at the point of pressing, together with the speed of rotation of the tablets press 1 is a criterion for how often a measurement must be triggered. When an exactly defined position on the tablet (e.g. the central point of the surface visible from above) enters the NIR beam, this determines the exact starting time of the measurement, the trigger time.

The time interval between two measurements is defined by the temporal intervals of the trigger times. The integration period is started with a trigger, which is automatically calculated and triggered via the mentioned properties and settings (speed, dimensions, etc.) of the tablets press 1 or alternatively is triggered by a light barrier when a tablet 9 passes a certain position.

The radiation receiving device 11 receives the radiation reflected from the tablet, which, for example, is guided by a light guide 12 to the spectrometer 13. The spectrometer 13 provides an output signal at a number of different wavelengths depending on the intensity of the received radiation. This takes place such that the spectrometer 13 splits the received radiation into a number of wavelengths and the photodiode array 15 detects the radiation with a sufficiently high resolution. The current from each photodiode is integrated over a preselected time period (preferably less than 10 ms) and then converted into a digital signal using an analogue to digital (A/D) converter for being processed in the evaluation device 17.

Based on the output signal supplied at the different wavelengths, the content of the at least one substance contained in the tablet 9 is quantitatively determined in the evaluation device 17 using a mathematical method. The electronic system must be suitable to pick up the output signals from the array 15 within 1 ms. Suitable mathematical methods are methods of multivariate data analysis. Suitable methods are for example also the PLS (Partial Least Square) method or the Principal Component Analysis (PCA). These types of methods are known to the person skilled in the art.

With these methods generally the deviations between a model spectrum obtained by a known method and the spectrum of the tablet to be measured are calculated at each measured wavelength. If these deviations exceed a set limit, then the tablet is detected as being significantly different from the model.

The mathematical methods can use weighting factors to reduce the effect of interfering variances in the NIR spectra, which are not resulting from the tablet composition, during the evaluation and to peak spectral features, which do not vary between samples of the same type of tablet.

Usually, at least one prior control measurement is carried out in which the content of the at least one substance in the tablet is quantitatively determined by an alternative recognised method.

The implementation of the method can use the mathematical method described in EP-B-0 887 638 on page 5, line 47 to page 8, line 12. EP-B-0 887 638 is in this respect included fully in the present description. The mathematical method described there uses weighting factors.

Subsequently, the result of the integrity test can be used, for example, to sort out unsuitable tablets 9 or to stop the complete manufacturing process.

With the described tablets press comprising an integral measuring device the manufacture and analysis of up to 1,000,000 tablets per hour can take place, wherein the data of a tablet are processed within a time frame of less than 10 ms, preferably less than 7 ms and more preferably less than 2 ms.

The tablets press according to the invention comprising an integral measuring device thus enables the analysis of all pressed tablets in real time with the same speed at which tablets have until now only been pressed. Thus, a device is provided with which 100% of all pressed tablets can be subjected to a detailed contact-free quality control directly after the manufacturing process.

The invention claimed is:

1. Tablets press with integral measuring device for the determination of the quantitative content of at least one substance in a pressed tablet, comprising:
   at least one radiation source, which emits radiation in the near infrared range, for irradiating the tablet;
   a radiation receiving device, which is contained in a measuring head (5) and receives the radiation reflected by the tablet;
   a spectrometer for receiving the radiation from the radiation receiving device and for supplying an output signal according to the intensity of the received radiation at a number of different wavelengths; and
   a device for the quantitative determination of the content of at least one substance contained in the tablet and/or for the determination of the ratios of all or some contained components based on the output signal;
   wherein the measuring device is suitable for measuring each single pressed tablet and the trigger times of the measurements are correlated with the conveying speed of the tablets press.

2. Tablets press according to claim 1, wherein the spectrometer comprises a device for splitting the received radiation into a number of wavelengths for detection by a photodiode array.

3. Tablets press according to claim 1, wherein the radiation source is a mercury halogen lamp.

4. Tablets press according to claim 1, wherein the spectrometer is suitable for carrying out a measurement within 2 ins.

5. Tablets press according to claim 1, wherein the measuring device is suitable for processing a trigger signal at least every 10 ins.

6. Tablets press according to claim 1, wherein the trigger times of the measurements can be determined automatically from the speed of the tablets press.

7. Tablets press according to claim 1, wherein the measuring head is arranged such that the measurement is performed between the release of the tablet by the press punches and the ejection of the tablet.

\* \* \* \* \*

UNITED STATES PATENT AND TRADEMARK OFFICE
CERTIFICATE OF CORRECTION

PATENT NO. : 7,294,837 B2
APPLICATION NO. : 11/133830
DATED : November 13, 2007
INVENTOR(S) : Richard Mertens and Heino Prinz It is certified that error appears in the above-identified patent and that said Letters Patent is hereby corrected as shown below:

Column 1, line 44, "test. chromatographical" should read -- test. Chromatographical --;

Column 5, lines 35 through 36, "recognised" should read -- recognized --;

Column 6, claim 4, line 3, "ins" should read -- ms --; and

Column 6, claim 5, line 3, "ins" should read -- ms --.

Signed and Sealed this

Twentieth Day of May, 2008

JON W. DUDAS
*Director of the United States Patent and Trademark Office*